United States Patent [19]

Besocke

[11] Patent Number: 4,686,847

[45] Date of Patent: Aug. 18, 1987

[54] METHOD AND VIBRATING CAPACITOR APPARATUS FOR ANALYSIS OF A SUBSTANCE OR OF AT LEAST ONE COMPONENT OF A MIXTURE OF SUBSTANCES

[75] Inventor: Karl-Heinz Besocke, Jülich, Fed. Rep. of Germany

[73] Assignee: Kernforschungsanlage Jülich Gesellschaft mit beschränkter Haftung, Jülich, Fed. Rep. of Germany

[21] Appl. No.: 787,264

[22] Filed: Oct. 15, 1985

[30] Foreign Application Priority Data

Oct. 20, 1984 [DE] Fed. Rep. of Germany ....... 3438546

[51] Int. Cl.$^4$ .............................................. G01N 27/22
[52] U.S. Cl. ................................. 73/23; 324/61 R; 361/289
[58] Field of Search ............... 73/23; 324/61 R, 61 P; 361/289, 290, 291, 286, 285, 279; 310/317, 321

[56] References Cited

U.S. PATENT DOCUMENTS

| | | | |
|---|---|---|---|
| 3,031,616 | 4/1962 | Hummel | 73/23 |
| 3,039,053 | 6/1962 | Jacobson | 73/23 |
| 3,166,696 | 1/1965 | Furman | 361/289 |
| 3,189,802 | 6/1965 | Zisman | 361/289 |
| 4,100,442 | 7/1978 | Besocke | 310/321 |
| 4,387,369 | 6/1983 | Klein et al. | 324/61 R |
| 4,409,509 | 10/1983 | Besocke et al. | 310/321 |

*Primary Examiner*—Stewart J. Levy
*Assistant Examiner*—Joseph W. Roskos
*Attorney, Agent, or Firm*—Frishauf, Holtz, Goodman & Woodward

[57] ABSTRACT

One or both plates of a capacitor, caused to vibrate so as to permit measurement of the contact potential between the electrodes, is coated with a sensor material for which the electron work function, and therefore the related contact potential, are sensitive to adsorption of a particular substance to be detected and measured in a gas or liquid to be analyzed. Two different materials may respectively be provided on the fixed and movable electrodes of the capacitor, for example nickel and molybdenum for measurement of ammonia content in air. The gas or liquid to be analyzed is introduced into a chamber in which the sensitized vibrating capacitor is located. Different substances can be detected and measured with the same sensor material if the temperature in the chamber is caused to run up or down through a temperature range and if the substances to be detected affect the sensor work function at different temperatures. An electrode carrier can also be subdivided into portions covered with different sensor materials by which different substances can be measured either sequentially or simultaneously. Continuous measurements can be made if the gas or liquid is passed through the chamber.

2 Claims, 6 Drawing Figures

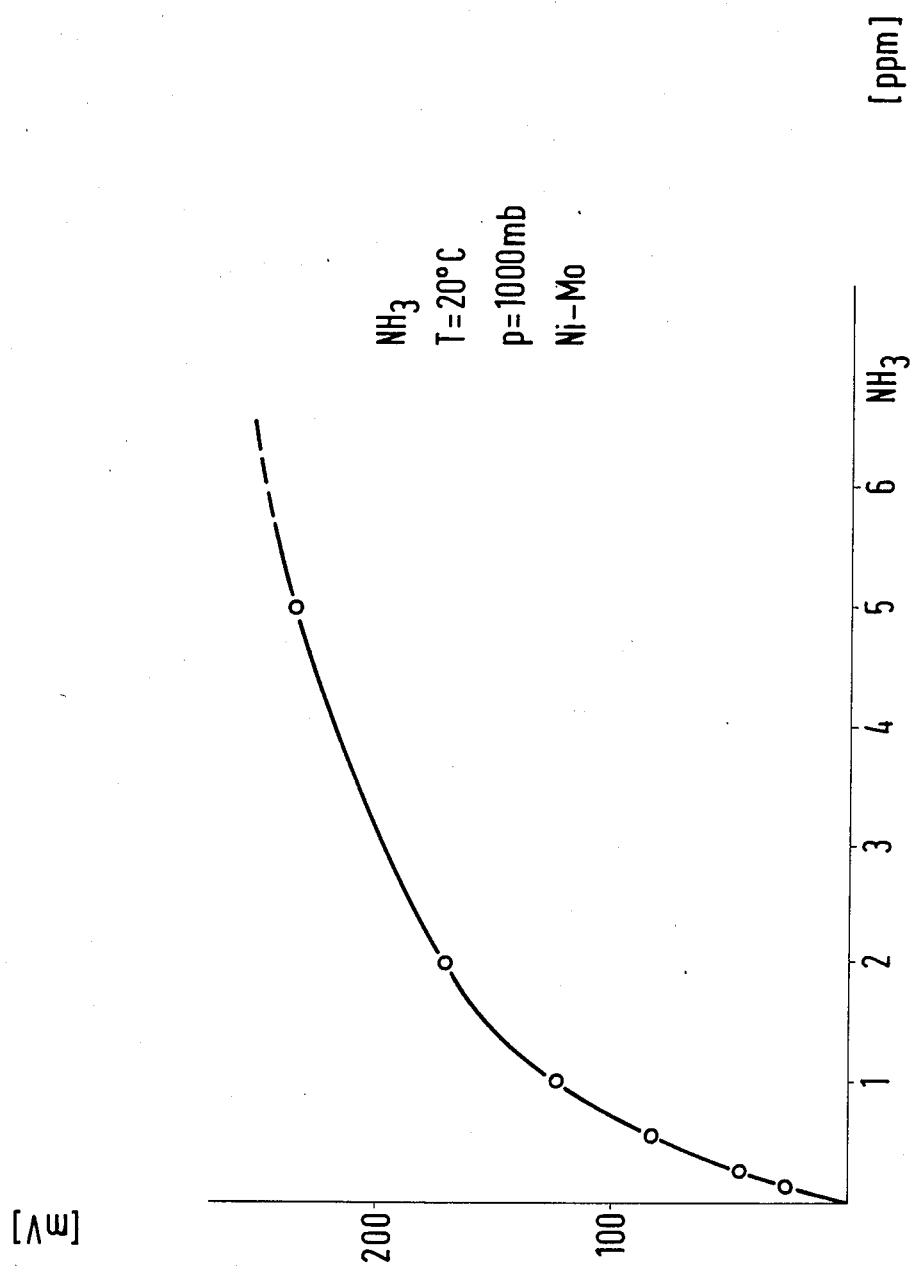

METHOD AND VIBRATING CAPACITOR APPARATUS FOR ANALYSIS OF A SUBSTANCE OR OF AT LEAST ONE COMPONENT OF A MIXTURE OF SUBSTANCES

The invention concerns analysis of a substance or of components of mixtures by measurement of the electron work function at surfaces or boundaries, particularly by means of electrodes that are movable with respect to each other so that their spacing can be made to vary in an oscillatory manner.

The analysis of substances or components of materials, especially in gas mixtures, involves difficulties especially if the substances or components are present in small concentrations in a gas mixture. Gas sensors of known types relate to the principles of measuring optical constants, measuring of chemical reactions, gas chromatography or measurement of changes in conductivity as set forth, for example, in "Sensors and Actuators" by G. Heiland, Vol. 2, pages 343–361 (1982). In those methods, however, the necessary selectivity, sensitivity and accuracy as well as the stability of the indications over long operating times are fulfilled only to a quite unsatisfactory degree.

SUMMARY OF THE INVENTION

It is an object of the present invention to provide a method and apparatus to obtain optimal fulfillment of the above-mentioned requirements regarding selectivity and sensitivity in the analysis of substances and to do so at small expense.

The invention is based on the recognition that the substances or material components of a mixture of gases or liquids can react with the surface of a sensor and that the modification caused by the adsorption of atoms and molecules on the surface of the sensor thus produced results in a change of the electronic state of surface atoms which in turn has the consequence of changing the so-called electron work function of the surface, namely the work necessary to draw an electron out of the sensor material.

Briefly, the electron work function of a sensor material which changes due to the adsorption of atoms and molecules of the substance to be detected is measured. The sensor material can be chosen to be selective in such a way that only a particular atom group or molecule group can produce a measurable change of the electron work function and thus provide a specific sensitivity for a substance or for a substance component of a gas or a liquid mixture. In accordance with this principle, substances in gas or liquid mixtures can be analyzed and even the degree of humidity can be measured.

In a further development of the invention, the electron work function is measured by the measurement of the contact potential between two electrodes moving relatively to each other, of which at least one is coated with sensor material. The change of the contact potential difference between electrodes can be determined by means of the vibrating capacitor method.

The accuracy of the measurement values can be optimized by constraining the substance or mixture of substances to pass by or arrive at the surface of the sensor material. In order to improve the sensitivity and selectivity, the sensor material is set or maintained at a predetermined temperature. It can also be useful to heat or cool the sensor material so that it runs through a temperature region during the adsorption phase for analysis of substances. The course of the temperature can be controlled by the running of a suitable program. Running through a predetermined temperature region raises the accuracy and selectivity of the analysis for such substances or mixture components which affect the electron work function to an extreme extent within the particular temperature range.

A vibrating capacitor with electrodes movable relative to each other is used as the measuring instrument for carrying out the measurement method. At least one of the electrodes carries a sensor material which reacts with the substances or one of the components of the substance mixture. Vibrating capacitors of this kind are known from German Pat. No. 2,613,528, German Published Patent Application No. 3,034,390, U.S. Pat. Nos. 4,100,442, and 4,409,509.

BRIEF DESCRIPTION OF THE DRAWINGS

The invention is further described by way of illustrative example with reference to the annexed drawings, in which:

FIG. 3 is a graph of contact potential measurements between a Ni and a Mo electrode exposed to air containing a concentration of $NH_3$ which continually increased during the measurements.

DESCRIPTION OF THE ILLUSTRATED EMBODIMENTS

Figure 1A:
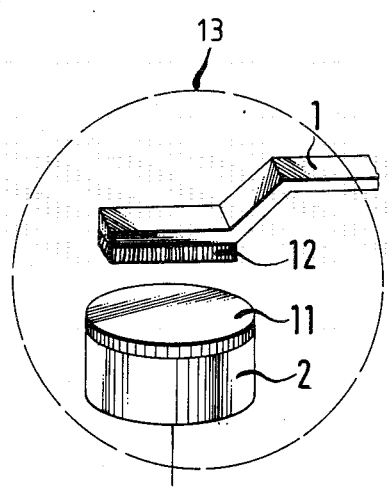
FIG. 1a is a detail of the capacitor portion of the vibratory capacitor shown in FIG. 1.
Figure 1:
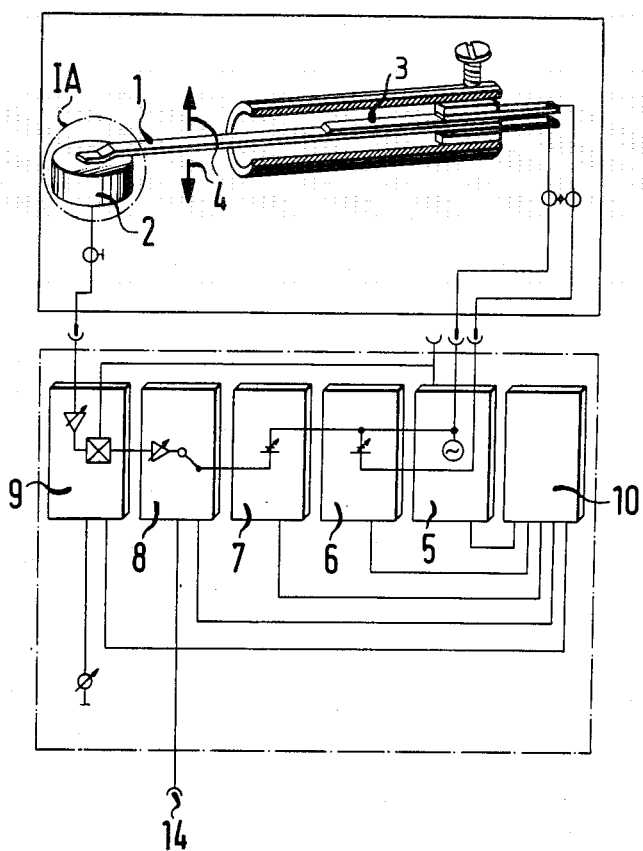
FIG. 1 is a diagram of a vibratory capacitor, illustrated in perspective, partly cut away, connected to a drive unit shown in circuit block diagram.

FIG. 1 shows a vibrating capacitor in the form known as a Kelvin probe. In this vibrating capacitor a piezoelectric unit 3 excites the oscillatory movements of a vibrating electrode 1 opposite an electrode 2 which is fixed in place. The direction of vibration 4 of the electrode 1 relative to the surface of the fixed electrode 2 is indicated by the double arrow drawn in FIG. 1.

An oscillator 7 provides the drive of the piezoelectric unit 3. The oscillator is controlled by a regulator 6. The signal passes a current sensitive lock-in amplifier 9, an integrator 8 and a compensation voltage circuit 7 in a well-known way. All electrical parts are supplied with energy necessary for their operation by a current supply 10. The average electrode spacing between the vibrating electrode 1 and the fixed electrode 2 is adjustable by means of the regulator 6. For this purpose a d.c. voltage is superimposed on the alternating voltage generated by the oscillator 5 for exciting the vibrating electrode 1.

FIG. 1a which is a magnified detail view of the electrodes 1 and 2 of FIG. 1 illustrates the application of the sensor material to vibrating and fixed electrodes. In the example illustrated in FIG. 1, one sensor material 11 is applied to the fixed electrode and another sensor material 12 is applied to the vibrating electrode. This serves for increasing the selectivity of the measurement and amplification of the sensitivity with which the vibrating capacitor reacts to substances or mixture components which are introduced into a measuring chamber 13 surrounding the vibrating capacitor. The subject of the coating of the electrodes with sensor material will be further explained in connection with the illustrative embodiments shown in FIG. 2.

A piezoelectric drive is not necessary for operating the vibrating capacitor. The drive can also operate electromagnetically or in some other known way.

The measuring chamber 13 can be fitted in its configuration in various ways to the conditions of operation. It can be designed even for microvolumes of less than 1 mm$^3$. The medium to be investigated can flow freely through the chamber or can be forced through it in order to facilitate a continuous measurement. In the case of forced flow a device for measuring the flow of the gas or liquid would normally be provided. That device can for example be disposed in the inlet to the measuring chamber for the gas or liquid mixture (see 43 in FIG. 1).

The measurement signal can in general be obtained from the fixed electrode and further processed by means of an electronic measurement amplifier for utilization of the output to produce an indication of the measurement or produce a signal for control or regulation purposes. For this purpose in the embodiment of FIG. 1 there is provided a connection 14 at the output of the integrator 8 either for an indicator device or for connection to a following data evaluating and processing apparatus.

The sensor materials 11 and 12 can be constituted either massively as electrode parts or applied as foils or as a thin layer on the electrodes 1 and 2. At least one of the electrodes 1 and 2 needs to operate as a sensor which responds specifically to one component of a gas or liquid under investigation. The other electrode can then consist, for example, of a chemically stable material (reference material) which does not change under exposure of the medium to be investigated.

Figure 2A:
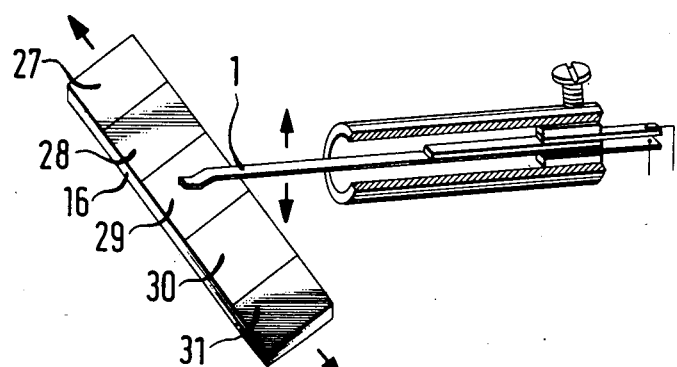
FIGS. 2a, 2b and 2c respectively show, in schematic perspective, various embodiments of fixed electrodes coated with different sensor materials, for use with a vibratory electrode.

For raising the selectivity and the sensitivity, the second electrode can also be provided with another sensor material reacting to the same substance. In order to make possible the analysis of different gas and liquid components, fixed electrodes 16, 17 and 18 are shown respectively in FIGS. 2a, 2b, and 2c which are subdivided into several partial electrodes, each of which is coated with a different sensor material that is affected specifically by a different component. This subdivision of the electrodes can be provided in various ways. In FIG. 2a there is shown an electrode 16 in the configuration of a sensor slide, in FIG. 2b an electrode 17 in the configuration of a revolving sensor wheel, rotatable stepwise, for instance, in the manner of the chambers of a revolver, and in FIG. 2c a fixed electrode 18 having a disk divided into sectors 19, 20, 21 and 22 coated with different sensor materials. Separate measurement leads 23, 24, 25 and 26 are connected to the respective sectors, so that the electron work functions of each sector can be separately measured during the movement of the vibrating electrode 1 which covers all of the sectors 19–22. The various material components of the gaseous or liquid mixture brought into contact with the fixed electrode can thus be simultaneously detected and measured by means of the various sensor materials. By means of a data processing apparatus for evaluating the measurement values a detailed analysis of the gas mixture and its component substances can be carried out.

Figure 2B:
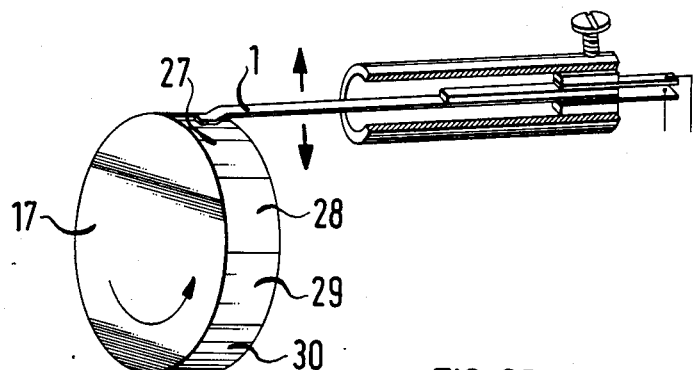
Figure 2C:
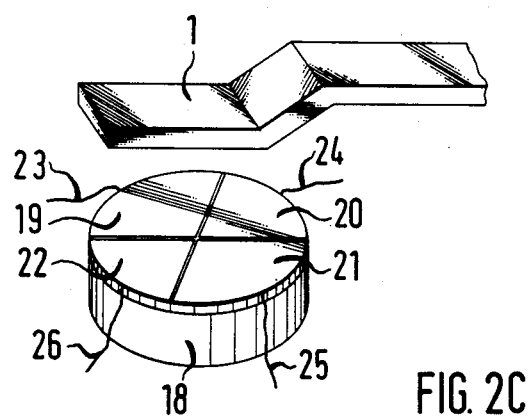

In contrast to the arrangement of FIG. 2c, the sensor slide coated with sensor materials 27–31 of FIG. 2a or the sensor revolver of FIG. 2b can be used only for successive detection and measurement of one specific component substance after another. In each of these steps, one of these sensor materials can have its electron work function measured during oscillation of the vibratory electrode 1. The measurements for each substance or component can thus proceed separately one from the other.

In order to regenerate the sensor materials or even to control the selectivity, it is possible to control the temperature of the sensor material by means of a heating device illustrated symbolically by the electrical resistance heating coil 44 in FIG. 1a, or by means of a cooling system, symbolized by the cooling coils 45 of FIG. 1a, which can likewise be used for controlling the temperature of the sensor material for the purposes just mentioned. Of course the heating coil is shown in FIG. 1a merely to simplify the drawing and may be actually located inside the measuring chamber or applied to the exterior of the measuring chamber walls, as is true also of the cooling coil 45.

A graph illustrating use of the invention is shown in FIG. 3 and represents measurement by means of the apparatus illustrated in FIG. 1. On this graph are plotted the contact potential in millivolts (mV) as a function of the concentration of ammonia NH$_3$ in air, given in parts per million (ppm). The measurements were made with nickel and molybdenum as sensor materials, with nickel being used for the fixed electrode 2 and molybdenum for the vibratory electrode 1. It makes no difference, however, for the analysis which of these sensor materials is fixed on the fixed electrode and which on the vibratory electrode, what is important being the pairing of the sensor materials for the contact potential difference to be measured.

In FIG. 3 the NH$_3$ concentration in ppm is plotted on the abscissa and the contact potential difference in mV on the ordinate for an example of analysis in which a chamber filled with air had the concentration of ammonia therein raised stepwise at an aggregate pressure of 1000 mb and a temperature of about 20° C. The vibrating capacitor in the chamber reacted to the rising ammonia concentration. With increasing ammonia concentration the measured contact potential rose. A stronger change of the contact potential occurred in the region of small ammonia concentration than in the region of higher ammonia concentration. Very small concentrations of substances can accordingly be measured at higher sensitivity.

A large number of sensor materials for detecting various substances are known from the technical literature which have the property that a change of the electron work function or a change of the surface potential can be used for an analysis of substances in gas or liquid form. It is also known that the sensitivity of the sensor material for various different substance components depends strongly upon the temperature (cf. the already mentioned publication of G. Heiland, "Sensors and Actuators", Vol. 2 (1982), p. 353). This information can be utilized for selective measurement of individual component substances of a mixture by a sensor material in such a manner that the sensor material is made to run through a predetermined temperature region that is so chosen that the component substances to be detected and measured have characteristic parameters, for example extreme values, that lie within this range of temperatures (cf. G. Heiland loc. cit., FIG. 11). Thus with a single sensor material analysis can be carried out for different substances.

Although the invention has been described with reference to particular illustrated examples, it will be understood that variations and modifications are possible within the inventive concept.

I claim:

1. Vibratory capacitor apparatus for measurement of the electron work function from surfaces or boundary areas, said apparatus having two electrodes that are movable relative one to the other and further comprising:

a surface layer applied onto at least one of said electrodes, facing the other of said electrodes and consisting of a sensor material of which the electron work function is affected by a substance to be detected in a gas or liquid, said sensor material being different from the material of the electrode on which it is applied; at least one of said electrodes having a said sensor material surface layer thereon also having a plurality of electrode portions, each of which is provided with a said sensor material layer, the sensor materials of the respective electrode portions being different, and means for causing a gas or liquid to come in contact with said electrodes, means for producing vibratory movement of at least one of said electrodes towards and away from the other of said electrodes and means for measuring contact potential between said electrodes.

2. Vibratory capacitor apparatus according to claim 1, in which means are provided for utilizing said electrode portions interchangeably one by one for separate measurement with each of the respective sensor materials.

* * * * *